US00PP34055P2

(12) United States Plant Patent
Van Swieten

(10) Patent No.: US PP34,055 P2
(45) Date of Patent: Mar. 22, 2022

(54) ***PHALAENOPSIS* ORCHID PLANT NAMED 'PHA1577644'**

(50) Latin Name: ***Phalaenopsis* hybrid**
Varietal Denomination: PHA1577644

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,846

(22) Filed: Nov. 23, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

(56) References Cited

PUBLICATIONS

PLUTO UPOVROM Plant Variety Database 20211217 Citation for 'PHA1577644' as per QZ PBR 2020/2309; Feb. 15, 2020; 1 page.*

* cited by examiner

*Primary Examiner* — Kent L Bell
(74) *Attorney, Agent, or Firm* — Jondle & Associates, P.C.

(57) ABSTRACT

A new and distinct variety of *Phalaenopsis* plant named 'PHA1577644', particularly characterized by having reddish-purple flowers with reddish-purple lips, flowers that are concave in lateral view, leaves with a semi-erect to horizontal attitude, and is propagated by meristem tissue culture, is disclosed.

3 Drawing Sheets

Genus and species: *Phalaenopsis* hybrid.
Variety denomination: 'PHA1577644'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA1577644'.

The new *Phalaenopsis* plant is a product of a planned breeding program conducted by the inventor in Bleiswijk, the Netherlands. The objective of this breeding program was to create a new *Phalaenopsis* plant with numerous attractive reddish-purple flowers with reddish-purple lips, suitable for potted plant production.

The new *Phalaenopsis* plant 'PHA1577644' is a result of cross-pollination made by the inventor in February 2013 in Bleiswijk, the Netherlands, of the proprietary female, or seed parent, *Phalaenopsis* hybrid '41922-02' (unpatented) with the proprietary male, or pollen parent, *Phalaenopsis* hybrid '32759-02' (unpatented).

The new *Phalaenopsis* was selected by the inventor as a single plant within the progeny of the stated cross-pollination in a controlled greenhouse in Bleiswijk, the Netherlands, in January 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 22, 2020 (Application no. 2020/2309), by Applicant who obtained the subject matter disclosed directly from the inventor. 'PHA1577644' has not been made publicly available or sold anywhere in the world prior to the effective filing date of this application with the exception of sales or disclosures made one year or less before the effective filing date of this claimed invention by Applicant who obtained 'PHA1577644' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA1577644' as a new and distinct variety of *Phalaenopsis* plant:

1) Reddish-purple flowers with reddish-purple lips;
2) Flower shape in lateral view is concave; and
3) Leaf attitude is semi-erect to horizontal.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in September 2021. Colors in the photographs may differ from the color values cited in the detailed botanical description, which accurately describe the actual colors of the new variety.

DESCRIPTION OF THE NEW VARIETY

Figure 1:
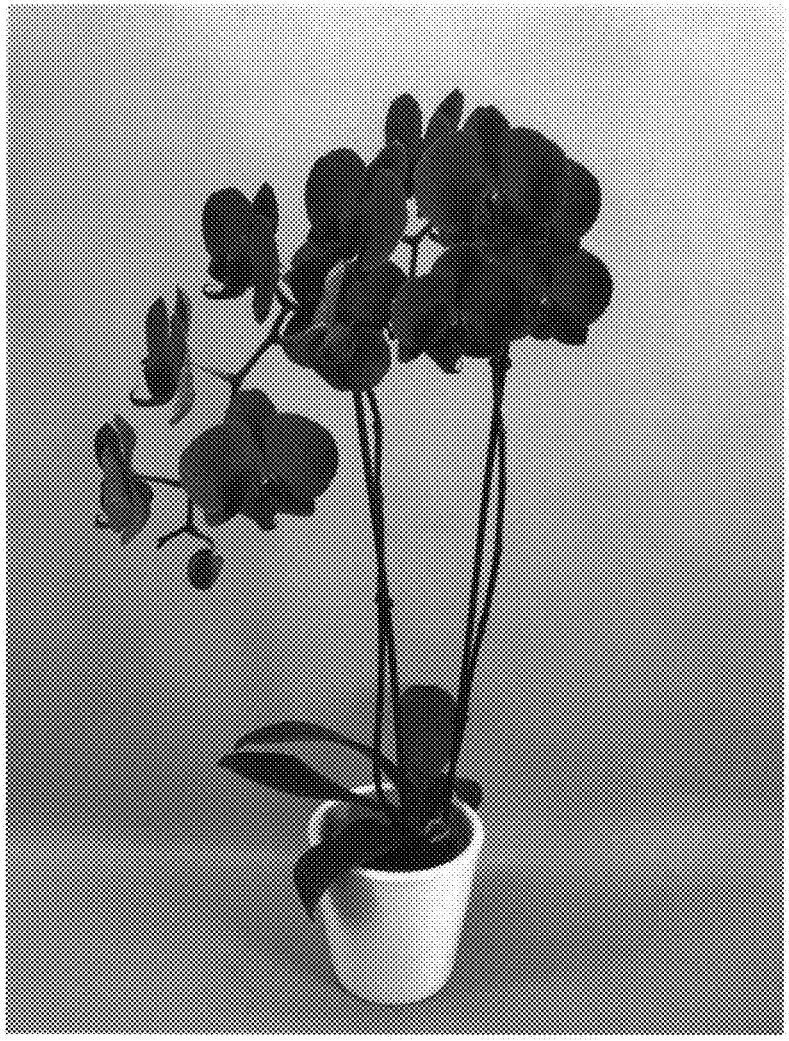
FIG. 1 shows the overall plant habit, including blooms, buds, and foliage of 'PHA1577644'.
Figure 2:
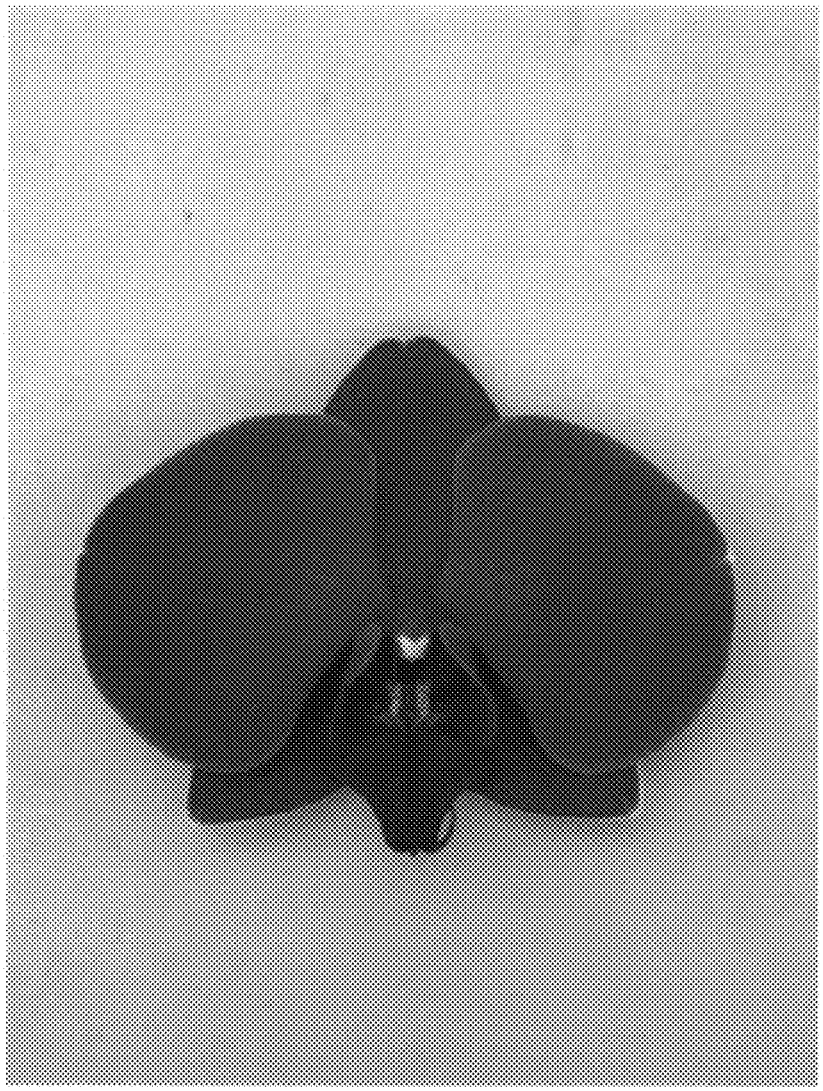
FIG. 2 shows a close-up of a flower of 'PHA1577644'.
Figure 3:
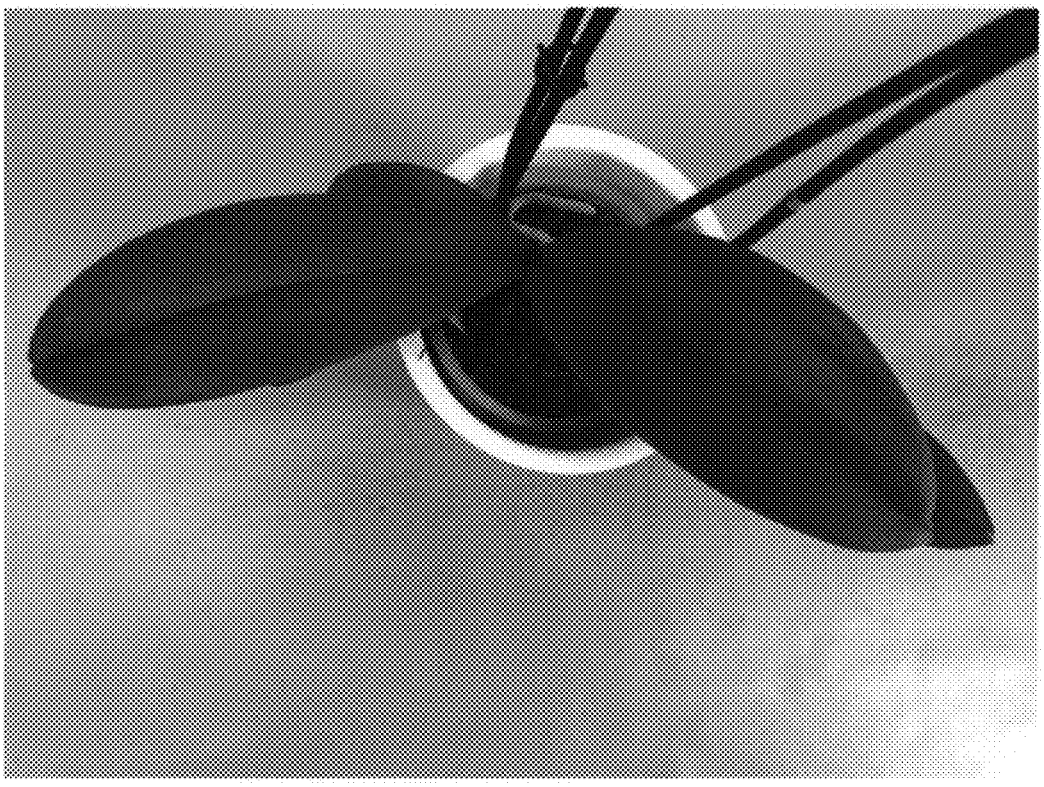
FIG. 3 shows an overhead view of the leaves of 'PHA1577644'.

The following detailed description sets forth the distinctive characteristics of 'PHA1577644'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in September 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHA1577644'.

Parentage:
- *Female parent*.—*Phalaenopsis* cultivar '41922-02' (unpatented).
- *Male parent*.—*Phalaenopsis* cultivar '32759-02' (unpatented).

Propagation:
- *Type*.—Meristem tissue culture.

Roots:
- *Root description*.—Greyed-green (a color in between RHS 190B and RHS 190C) colored roots with branching lateral roots having yellow-green (RHS 146C) with a touch of purplish-red (RHS N77B) colored root tips.

Plant:
- *Crop time to flowering*.—Following asexual propagation (in vitro), the rooted cuttings grow for 20-24 weeks. After transplantation into 12-cm pots, the plants are finished after 48 to 50 weeks.
- *Growth habit of the peduncle*.—Upright to slightly pendent with raceme inflorescence.
- *Height* (*from soil level to top of inflorescence*).—Approximately 62.0 cm to 67.0 cm.
- *Width* (*measured from leaf tips*).—About 31.0 cm to 34.0 cm.
- *Vigor*.—Strong.

Leaves:
- *Mature leaves*.—Quantity per plant: 6 to 7 leaves are produced before flowering. Length (fully expanded): 17.0 cm to 19.0 cm. Width: 6.5 cm to 7.5 cm. Position of the broadest part of the leaf: At the middle. Shape: Oblong. Base shape: Moderately elongated. Apex: Obtuse asymmetric. Leaf blade angle with the petiole (measured from the horizontal position): Between 20 degrees and 40 degrees. Leaf margin: Entire. Color: Upper surface: RHS 146A with a dark purplish-red margin (RHS N79B) toward the tip. Lower surface: RHS 146B with a dark red-purple margin and shade (a color in between RHS N79A and RHS 187A) toward the tip. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B with a hint of dark purplish-red (RHS N79B).

Peduncle:
- *Quantity per plant*.—1 to 2.
- *Number of flowers per peduncle*.—8 to 10.
- *Length*.—62.0 cm to 67.0 cm.
- *Diameter*.—4.0 mm to 5.0 mm.
- *Strength*.—Strong.
- *Aspect*.—Upright to slightly pendent.
- *Texture*.—Smooth.
- *Color*.—Brown (RHS 200A) with a touch of yellow-green (RHS 146D).
- *Internode length*.—4.0 cm to 5.0 cm.

Inflorescence description:
- *Appearance*.—Upright to slightly pendent, raceme inflorescence with bilaterally symmetrical flowers that open in succession beginning with the lowermost flower.
- *Number of inflorescences*.—1 to 2.
- *Inflorescence size*.—Height (from base to tip): 230.0 mm to 260.0 mm.
- *Flowering time*.—First flowers can be expected 10 to 11 months after planting in a 12-cm pot.
- *Flower*.—Height: 68.0 mm to 73.0 mm. Diameter: 83.0 mm to 88.0 mm. Depth of lip: 23.0 mm to 25.0 mm.
- *Flower shape*.—Concave.
- *Flower longevity*.—On the plant: 14 to 16 weeks.
- *Fragrance*.—Absent.
- *Flower bud*.—Average size: Medium to large. Length: 23.0 mm to 25.0 mm. Width: 19.0 mm to 21.0 mm. Shape: Egg shaped. Color: Yellow-green (RHS 146D) at the base with a dark purple-red shade (a color in between RHS N79B and RHS N77B).
- *Petals*.—Arrangement: Open/free. Shape: Semi-circular. Apex: Rounded asymmetric. Margin: Entire. Length (from base to tip): 39.0 mm to 41.0 mm. Width: 52.0 mm to 54.0 mm. Position of the broadest part of the petal: Toward the base. Color (when fully opened): Upper surface: Basic color: Reddish-purple (RHS N78A). Over color: Light reddish-purple dots (RHS N78A) toward base; dark reddish-purple stripes (a color in between RHS N79C and RHS N78A) toward the tip. Lower surface: Basic color: Reddish-purple (RHS N78B). Over color: Reddish-purple shade (RHS N78A). Number of spots, dots, and stripes on the petals (upper surface): Few to medium small dots; medium stripes. Color of spots, dots, and stripes on the petals (upper surface): Dots (RHS N78D); stripes (a color in between RHS N79C and RHS N78A). Density of netting of the petals (upper surface): None. Color of the netting (upper surface): Not applicable.
- *Dorsal sepal*.—Shape: Elliptic. Apex: Emarginated symmetric. Margin: Entire. Length (from base to tip): 41.0 mm to 43.0 mm. Width: 33.0 mm to 35.0 mm. Position of the broadest part of the dorsal sepals: At the middle. Color (when fully opened): Upper surface: Basic color: Reddish-purple (RHS N78A). Over color: Dark purplish-red shade and stripes (RHS N79C) and very small light reddish-purple dots (RHS N78D). Lower surface: Basic color: Reddish-purple (RHS N78B). Over color: Yellowish-green (RHS 195B) at the middle from the base. Number of spots, dots, and stripes on the dorsal sepals (upper surface): Medium stripes; medium of very small dots. Color of spots, dots, and stripes on the dorsal sepals (upper surface): Stripes (RHS N79C); dots (RHS N78D). Density of netting of the dorsal sepals (upper surface): None. Color of the netting (upper surface): Not applicable.

*Lateral sepals*.—Shape: Ovate. Apex: Obtuse asymmetric. Margin: Entire. Length (from base to tip): 43.0 mm to 45.0 mm. Width: 30.0 mm to 32.0 mm. Position of the broadest part of the lateral sepals: Toward the base. Color (when fully opened): Upper surface: Basic color: Reddish-purple (RHS N78A). Over color: Touch of light yellow-green (RHS 145B) at the base; dark purplish-red stripes and dots (RHS N79C). Lower surface: Basic color: Reddish-purple (RHS N78B). Over color: Light yellow-green (RHS 145C) and purplish-pink shade (RHS N78C). Number of spots, dots, and stripes on the lateral sepals (upper surface): Few of very small dots at the base and medium to many stripes. Color of spots, dots, and stripes on the lateral sepals (upper surface): RHS N79C. Density of netting of the lateral sepals (upper surface): None. Color of the netting (upper surface): Not applicable.

*Labellum* (*lip*).—Whiskers: Present. Length of whiskers: 13.0 mm to 15.0 mm. Color of whiskers: Dark purplish-red (RHS N79C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 21.0 mm to 23.0 mm. Width: 14.0 mm to 16.0 mm. Color: Upper surface: Dark purplish-red (a color in between RHS N79C and RHS 71A). Lower surface: Touch of white (RHS NN155C) and greenish-yellow (RHS 6C) at the base; reddish-purple (RHS N78A) toward the tip; dark purplish-red stripes (a color in between RHS N79C and RHS 71A). Number of spots and stripes on the lateral lobe: Few stripes. Color of spots and stripes on the lateral lobe: A color in between RHS N79C and RHS 71A. Density of netting of the lateral lobe: None. Color of the netting: Not applicable.

*Apical lobe*.—Shape: Triangular. Margin: Entire. Length: 23.0 mm to 25.0 mm. Width: 23.0 mm to 25.0 mm. Color: Upper surface: Dark purplish-red (RHS N79C). Lower surface: Dark purplish-red (a color in between RHS N79C and RHS 71A). Number of spots and stripes on the apical lobe: None. Color of spots and stripes on the apical lobe: None. Density of netting of the apical lobe: None. Color of the netting: None. Bump and ridge: Medium.

*Callus*.—Average size: Large. Height: 8.0 mm to 9.0 mm. Length: 6.0 mm to 7.0 mm. Width: 4.0 mm to 5.0 mm. Color: Greenish-yellow tips (RHS 6C); greenish-white (RHS 157D) on sides; dotted (RHS 59A).

Reproductive organs:

*Column*.—Length: 10.0 mm to 11.0 mm. Diameter: 5.0 mm to 6.0 mm. Color: Reddish-purple (RHS N78A).

*Pollinia*.—Quantity: 2. Diameter: 1.0 mm to 1.2 mm. Color: Orange (RHS 24A).

*Ovary*.—Length: 12.0 mm to 14.0 mm. Diameter: 2.2 mm to 2.5 mm.

*Pedicel*.—Length: 38.0 mm to 40.0 mm. Diameter: 2.6 mm to 3.0 mm. Color: Yellow-green (RHS 146B and RHS 146D) with a touch of very light purple (RHS 76B) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA1577644' differs from the female parent plant '41922-02' (unpatented) in that 'PHA1577644' has flowers with an even pattern, whereas '41922-02' has flowers with a shaded pattern toward the center.

'PHA1577644' differs from the male parent plant '32759-02' (unpatented) in that 'PHA1577644' has dorsal sepals with a concave curvature of the longitudinal axis, whereas '32759-02' has dorsal sepals with a convex curvature of the longitudinal axis.

'PHA1577644' is most similar to the commercial *Phalaenopsis* plants named 'PHALGOCO' (U.S. Plant Pat. No. 32,247) and 'PHALDUKAI' (U.S. Plant Pat. No. 28,157). 'PHA1577644' differs from the commercial variety 'PHALGOCO' in that 'PHA1577644' has flowers that are concave in lateral view, triangular apical lobes, and leaves with a semi-erect to horizontal attitude, whereas 'PHALGOCO' has flowers that are flat in lateral view, trullate apical lobes, and leaves with a semi-drooping attitude.

'PHA1577644' differs from the commercial variety 'PHALDUKAI' in that 'PHA1577644' has strongly raised calluses and rounded petal apexes, whereas 'PHALDUKAI' has moderately raised calluses and mucronate petal apexes.

I claim:

1. A new and distinct variety of *Phalaenopsis* plant named 'PHA1577644', substantially as described and illustrated herein.

* * * * *